US010004873B1

(12) United States Patent
Hur et al.

(10) Patent No.: US 10,004,873 B1
(45) Date of Patent: Jun. 26, 2018

(54) SLEEP AID DEVICE FOR VEHICLE, SYSTEM INCLUDING SLEEP AID DEVICE, AND METHOD OF SLEEP AID FOR VEHICLE

(71) Applicants: HYUNDAI MOTOR COMPANY, Seoul (KR); KIA MOTORS CORPORATION, Seoul (KR)

(72) Inventors: Nam Woong Hur, Hwaseong-si (KR); Eung Hwan Kim, Seoul (KR); Seul Ki Jeon, Suwon-si (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 0 days. days.

(21) Appl. No.: 15/697,820

(22) Filed: Sep. 7, 2017

(30) Foreign Application Priority Data

Mar. 13, 2017 (KR) ........................ 10-2017-0031252

(51) Int. Cl.

| G08B 23/00 | (2006.01) |
|---|---|
| A61M 21/02 | (2006.01) |
| A61B 5/00 | (2006.01) |
| G08B 21/06 | (2006.01) |
| A61B 5/11 | (2006.01) |
| G05D 1/02 | (2006.01) |

(52) U.S. Cl.
CPC .............. *A61M 21/02* (2013.01); *A61B 5/11* (2013.01); *A61B 5/4812* (2013.01); *G05D 1/0274* (2013.01); *G08B 21/06* (2013.01); *G05D 2201/0213* (2013.01)

(58) Field of Classification Search
CPC .......... B60W 40/08; B60W 2040/0827; G08B 21/02; G01C 21/3469; G01C 21/3461
USPC .......................................... 340/575, 576, 438
See application file for complete search history.

(56) References Cited

U.S. PATENT DOCUMENTS

| 9,463,805 B2 * | 10/2016 | Kirsch ................. B60W 40/08 |
| 9,500,489 B1 * | 11/2016 | Ng ..................... G01C 21/3461 |
| 9,789,878 B2 * | 10/2017 | Lee ..................... B60W 40/08 |
| 2003/0088344 A1 | 5/2003 | Oda et al. |

(Continued)

FOREIGN PATENT DOCUMENTS

| JP | 2003141676 A | 5/2003 |
| JP | 2005310095 A | 11/2005 |

(Continued)

*Primary Examiner* — Hoi Lau
(74) *Attorney, Agent, or Firm* — McDermott Will & Emery LLP

(57) ABSTRACT

A sleep aid device for a vehicle includes a sleep information setting device for setting sleep information and a target sleep time of a user, a route establishing device for establishing a route to a destination and for calculating a time required to reach the destination, a sleep mode determining device for determining whether a current mode is a sleep mode and for determining a sleep-inducing start time using the sleep information and the time required to reach the destination, a sleep mode controller for controlling an intra-vehicle device in the sleep mode at the sleep-inducing start time, a wake-up mode determining device for determining a sleep state of the user and entering a wake-up mode when the user is in a light sleep state, and a wake-up mode controller for controlling the intra-vehicle device in the wake-up mode when the wake-up mode is entered.

20 Claims, 7 Drawing Sheets

(56) References Cited

U.S. PATENT DOCUMENTS

| | | | |
|---|---|---|---|
| 2005/0231342 A1 | 10/2005 | Kim | |
| 2015/0115481 A1 | 4/2015 | Jang et al. | |
| 2016/0046294 A1* | 2/2016 | Lee | B60W 40/08 |
| | | | 340/576 |
| 2016/0176409 A1* | 6/2016 | Kirsch | B60W 40/08 |
| | | | 701/37 |
| 2017/0108236 A1* | 4/2017 | Guan | F24F 11/0012 |

FOREIGN PATENT DOCUMENTS

| | | |
|---|---|---|
| JP | 2015131521 A | 7/2015 |
| KR | 100832883 B1 | 6/2008 |
| KR | 20130138009 A | 12/2013 |
| KR | 20150047253 A | 5/2015 |

\* cited by examiner

SLEEP AID DEVICE FOR VEHICLE, SYSTEM INCLUDING SLEEP AID DEVICE, AND METHOD OF SLEEP AID FOR VEHICLE

CROSS-REFERENCE TO RELATED APPLICATION

This application claims the benefit of priority to Korean Patent Application No. 10-2017-0031252, filed on Mar. 13, 2017 with the Korean Intellectual Property Office, the disclosure of which is incorporated herein in its entirety by reference.

TECHNICAL FIELD

The present disclosure relates to a sleep aid device for a vehicle, a system including the sleep aid device, and a method of sleep aid, and more particularly, to technologies for helping a user to engage in deep sleep during movement in an autonomous vehicle and wake up in a light sleep state at a time set to a target time by the user.

BACKGROUND

A possible spread of autonomous vehicles is expected to facilitate another operation other than a driving operation during movement of the vehicle. As a result of a survey, 25% of users responded that they would sleep in their autonomous vehicles.

However, sleep taken during movement of the autonomous vehicle is performed during a relatively short time, and there are potential distractions, such as vibrations and noises, during sleep. Further, since users may feel fatigued if they wake up during deep sleep, a wake-up time and period is important.

Thus, a wearable device, a smartphone, or the like may be used as a monitoring device for sleep aid operations. However, accuracy is reduced in such devices due to vibrations of a vehicle when the devices are used in the vehicle. The wearable device should be worn on the user, or an application should be executed in the smartphone to be placed at a specific location.

SUMMARY

The present disclosure has been made to solve the above-mentioned problems occurring in the prior art while advantages achieved by the prior art are maintained intact.

An aspect of the present disclosure provides a sleep aid device for a vehicle for helping a user to take deep sleep during movement and aiding him or her in waking up in a light sleep state at a time set to a target time, a system including the same, and a method therefor.

The technical problems to be solved by the present disclosure are not limited to the aforementioned problems, and any other technical problems not mentioned herein will be clearly understood from the following description by those skilled in the art to which the present disclosure pertains.

According to an aspect of the present disclosure, a sleep aid device for a vehicle may include: a sleep information setting device configured to set sleep information and a target sleep time of a user, a route establishing device configured to establish a route to a destination and calculate a time required to reach the destination, a sleep mode determining device configured to determine whether a current mode is a sleep mode and determine a sleep-inducing start time using the sleep information and the time required, a sleep mode controller configured to control an intra-vehicle device in the sleep mode at the sleep-inducing start time, a wake-up mode determining device configured to determine a sleep state of the user and enter a wake-up mode when the user is in a light sleep state, and a wake-up mode controller configured to control the intra-vehicle device in the wake-up mode when the wake-up mode is entered.

In an embodiment, the sleep information may include one or more of an amount of sleep of the user, quality of sleep of the user, and/or schedule information of the user.

In an embodiment, the sleep information setting device may be configured to receive the sleep information via one or more of a wearable device, a smart bed, and/or a smartphone or directly receive the sleep information from the user in the vehicle.

In an embodiment, the sleep information setting device may be configured to calculate the target sleep time using the sleep information.

In an embodiment, the sleep information setting device may be configured to receive the target sleep time in advance from the user or set the target sleep time to a previously stored recommendation value according to an age or gender of the user, if the target sleep time is not received in advance.

In an embodiment, the sleep mode determining device may be configured to determine whether the sleep mode is entered, using one or more of quality of sleep of the previous day of the user, a sleep time of the previous day, a sleep period of the previous day, and/or a schedule of the previous day.

In an embodiment, the route establishing device may be configured to establish the route again to adjust the time required in response to the target sleep time, if the target sleep time is shorter than the time required.

In an embodiment, the route establishing device may be configured to establish a shortest-distance or shortest-time route to the destination in the sleep mode, the route established by first searching for a road which facilitates cruise control.

In an embodiment, the intra-vehicle device may include one or more of a seat, an air conditioning device, a diffuser device, a light device, and/or a sound device.

In an embodiment, the sleep mode controller may be configured to flatten the seat, control the air conditioning device to set an indoor temperature of the vehicle to a sleep temperature, control the diffuser device to generate a sleep-inducing scent, turn off the light device to control the light device in a shade mode, or control the sound device to output one of a white noise, a natural sound, and/or a sleep-inducing beep sound.

In an embodiment, the wake-up mode determining device may be configured to enter the wake-up mode, if the vehicle will arrive at the destination within a time and if the user is in the light sleep state.

In an embodiment, the wake-up mode controller may be configured to turn on the light device, control the sound device to output an alarm sound or a natural sound, operate a massage device of the seat, control the diffuser device to generate a wake-up scent, or control the air conditioning device to generate cold wind, when the wake-up mode is entered.

According to another aspect of the present disclosure, a sleep aid system for a vehicle may include: a communication device configured to receive sleep information or a target sleep time from a user terminal, an input device configured to receive the target sleep time, the sleep information, and a destination from a user, a sleep aid device configured to establish a route to the destination, determine a sleep-inducing start time based on a time required to reach the destination and the target sleep time, control an intra-vehicle device in a sleep mode at the sleep-inducing start time, monitor a sleep state of the user and a destination arrival time, and control the intra-vehicle device in a wake-up mode if the vehicle will arrive at the destination within a time and if the user is in a light sleep state, and a storage device configured to store the target sleep time, the sleep information, and information about the route to the destination.

In an embodiment, the user terminal may include one or more of a wearable device, a smartphone, and/or a smart bed.

According to another aspect of the present disclosure, a sleep aid method for a vehicle may include: setting sleep information and a target sleep time of a user, establishing a route to a destination and calculating a time required to reach the destination, determining whether a current mode is a sleep mode and determine a sleep-inducing start time using the sleep information and the time required, controlling an intra-vehicle device in the sleep mode at the sleep-inducing start time, entering a wake-up mode, if the vehicle will arrive at the destination within a time and if the user is in a light sleep state, and controlling the intra-vehicle device in the wake-up mode when the wake-up mode is entered.

In an embodiment, the method may further include receiving the sleep information or the target sleep time from a smart device of the user, directly receive the sleep information or the target sleep time from the user, or using a previously stored recommendation value according to an age or gender of the user as the target sleep time.

In an embodiment, the determining of whether the current mode is the sleep mode and the determining of the sleep-inducing start time may include determining whether the sleep mode is entered, using one or more of quality of a past sleep of the user, a past sleep time, a past sleep period, and/or a past schedule.

In an embodiment, the establishing of the route to the destination and the calculating of the time required to reach the destination may include establishing the route again to adjust the time required in response to the target sleep time, if the target sleep time is shorter than the time required.

In an embodiment, the establishing of the route to the destination and the calculating of the time required to reach the destination may include establishing a shortest-distance or shortest-time route to the destination in the sleep mode, the route established by first searching for a road which facilitates cruise control.

In an embodiment, the controlling of the intra-vehicle device in the sleep mode may include flattening a seat, controlling an air conditioning device to set an indoor temperature of the vehicle to a sleep temperature, controlling a diffuser device to generate a sleep-inducing scent, or turning off a light device to control the light device in a shade mode.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Hereinafter, exemplary embodiments of the present disclosure will be described in detail with reference to the accompanying drawings. In adding reference denotations to elements of each drawing, although the same elements are displayed on a different drawing, it should be noted that the same elements have the same denotations in different drawings. In addition, in describing exemplary embodiments of the present disclosure, if it is determined that a detailed description of related well-known configurations or functions blurs the concepts of exemplary embodiments of the present disclosure, it will be omitted.

In describing elements of exemplary embodiments of the present disclosure, the terms $1^{st}$, $2^{nd}$, first, second, A, B, (a), (b), and the like may be used herein. These terms are only used to distinguish one element from another element, and do not limit the corresponding elements irrespective of the nature, turn, or order of the corresponding elements. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

Hereinafter, a description will be given in detail of exemplary embodiments of the present disclosure with reference to FIGS. 1 to 7.

Figure 1:
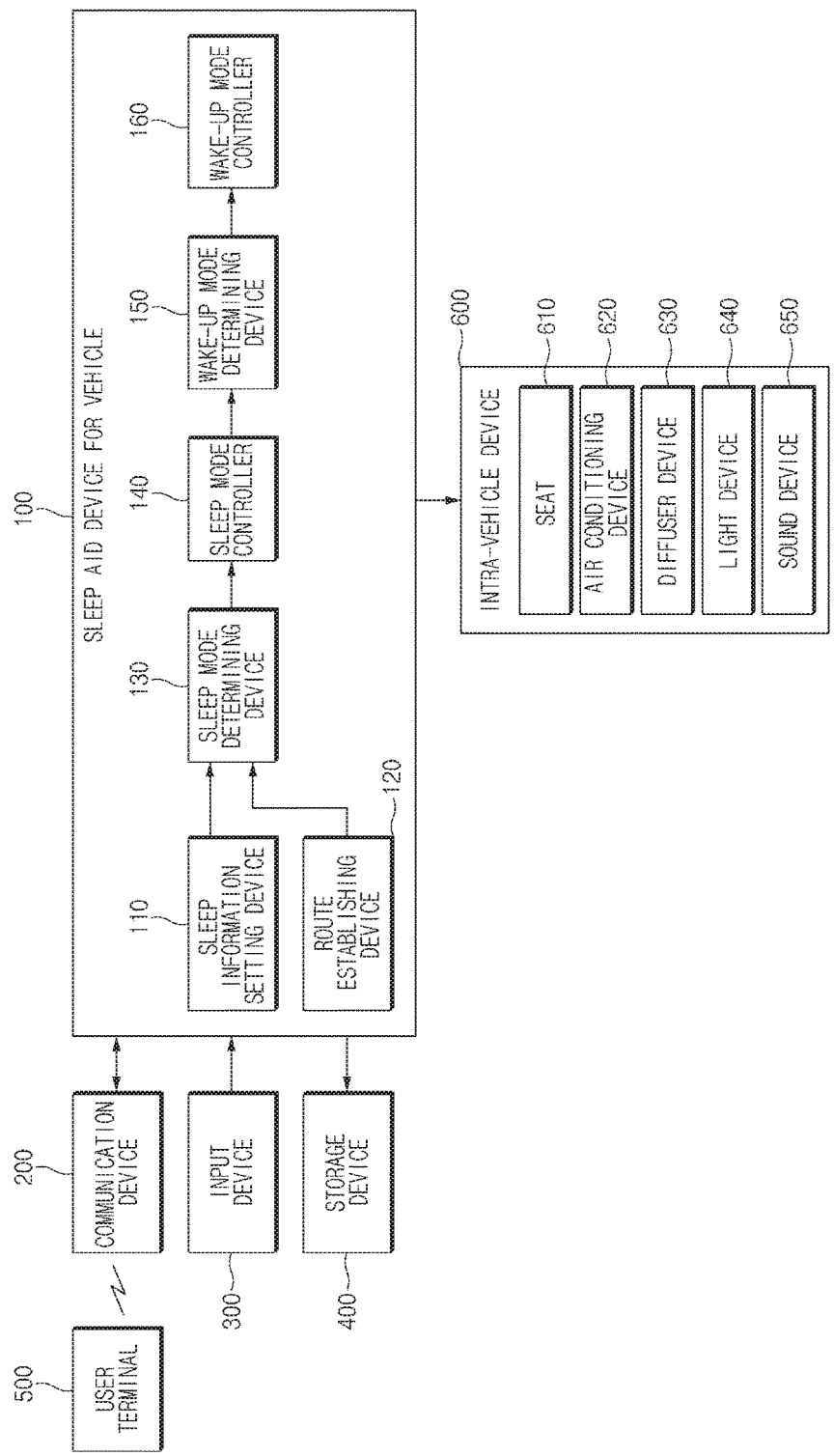
FIG. 1 is a block diagram illustrating a configuration of a sleep aid system for a vehicle according to exemplary embodiments of the present disclosure.

FIG. 1 is a block diagram illustrating a configuration of a sleep aid system for a vehicle according to exemplary embodiments of the present disclosure.

The sleep aid system for the vehicle according to exemplary embodiments of the present disclosure may include a sleep aid device 100 for the vehicle, a communication device 200, an input device 300 and a storage device 400.

The sleep aid device 100 may establish a route to a destination and may determine a sleep-inducing start time based on a time required to reach the destination and a target sleep time, thus controlling an intra-vehicle device 600 at the sleep-inducing start time. The sleep aid device 100 may monitor a sleep state of a user of the vehicle and a destination arrival time to control the intra-vehicle device 600 in a wake-up mode if the vehicle will arrive at the destination within a certain time and if the user is in a light sleep state.

For this purpose, the sleep aid device 100 may include a sleep information setting device 110, a route establishing device 120, a sleep mode determining device 130, a sleep mode controller 140, a wake-up mode determining device 150 and a wake-up mode controller 160.

The sleep information setting device 110 may set sleep information and a target sleep time of the user. Herein, the sleep information may include one or more of an amount of sleep of the user, quality of sleep of the user, schedule information of the user, where the target sleep time may be a sleep time needed by the user in the vehicle.

The sleep information setting device 110 may receive sleep information or a target sleep time from a user terminal 500. In this case, the user terminal 500 may include one or more of a wearable device worn on the user, a smart bed and/or a smartphone. Further, the sleep information setting device 110 may directly receive sleep information or a target sleep time in the vehicle.

Further, the sleep information setting device 110 may calculate a target sleep time using sleep information. In other words, the sleep information setting device 110 may calculate the target sleep time in consideration of an amount of past (the previous day) sleep, a past (the previous day) sleep period, and/or a past (the previous day) schedule and the like. For example, if an amount of sleep of the previous day is 3 hours, the sleep information setting device 110 may determine an amount of sleep as being insufficient and may set a target sleep time to be longer.

Further, the sleep information setting device 110 may receive a target sleep time in advance from the user. Alternatively, if the sleep information setting device 110 does not receive a target sleep time in advance, it may set a target sleep time to a previously stored recommendation value according to an age or gender of the user. For example, if the user is in his or her forties, since he or she may be more tired than users in their twenties, the sleep information setting device 110 may increase a sleep time for the user in his or her forties.

The route establishing device 120 may establish a route to the destination and may calculate a time required to reach the destination. In this case, the route establishing device 120 may directly receive the destination via an input device 300 from the user or may receive the destination from the user terminal 500.

If a target sleep time is shorter than a time required to reach the destination, since the user should wake up in a deep sleep state, the route establishing device 120 may establish a route again to adjust the time required in response to the target sleep time. For example, if the target sleep time is set to three hours and if the time required, or estimated to be required, to reach the destination is two hours, the route establishing device 120 may establish a route again to reach the destination after driving for three hours, or may establish a route that reaches the destination, or is estimated to reach the destination, in three hours.

Further, the route establishing device 120 may establish the shortest-distance or shortest-time route to the destination in a sleep mode, the route established by first searching for a road which facilitates cruise control. In other words, since it is advantageous for the user to take deep sleep on a straight road as compared a road with some or many corners, the route establishing device 120 may first search for a road which has a few corner and facilitates cruise control and may establish such a route, thus minimizing inconvenience by driving when the user sleeps.

Further, the route establishing device 120 may avoid a point where quality of sleep of the user is reduced, based on accumulated statistical information to generate a route.

The sleep mode determining device 130 may determine whether a current mode is a sleep mode and a sleep-inducing start time, using the sleep information and the time required.

In other words, the sleep mode determining device 130 may determine whether the vehicle enters the sleep mode using one or more of quality of sleep of the previous day of the user, a sleep time of the previous day, a sleep period of the previous day and/or a schedule of the previous day. Further, the sleep mode determining device 130 may determine whether a target sleep time according to sleep information is included in a time required. If the target sleep time is included in the time required, the vehicle may enter the sleep mode. Further, the sleep mode determining device 130 may determine a sleep-inducing start time in consideration of the time required and the target sleep time when the vehicle enters the sleep mode. For example, if the time required is 3 hours and if the target sleep time is 2 hours 30 minutes, the sleep mode determining device 130 may induce the vehicle to enter the sleep mode at a time of 20 minutes after the vehicle starts to drive.

The sleep mode controller 140 may control the intra-vehicle device 600 in the sleep mode at the sleep-inducing start time. In other words, the sleep mode controller 140 may flatten a seat 610 in the intra-vehicle device 600 and may operate a reclining seat and a lower shock absorption damper. Also, the sleep mode controller 140 may control an air conditioning device 620 to set an indoor temperature of the vehicle to a sleep temperature (e.g., 24 degrees) or may control a diffuser device 630 to generate a sleep-inducing scent such as a lavender scent.

Further, the sleep mode controller 140 may turn off a light device 640 and may control the light device 640 in a shade mode. The sleep mode controller 140 may control a sound device 650 to output a white noise, a natural sound, a sleep-inducing beep sound, music or the like.

If the vehicle will arrive at the destination within a time (e.g., 15 minutes to 20 minutes prior to an arrival time) and if the user is in a light sleep state, the wake-up mode determining device 150 may enter a wake-up mode.

In this case, the wake-up mode determining device 150 may monitor tossing and turning, breathing, and heartbeat of the user using the sensed results of pressure sensors installed on a surface of the seat 610 of the vehicle, a radar, and an ultrasonic sensor. If sleep depth is lowered although there is much, or a degree of, sleep time left during monitoring, the wake-up mode determining device 150 may request the sleep mode controller 140 to additionally perform a sleep-inducing operation. Further, the wake-up mode determining device 150 may monitor sleep depth for each location on a route, may store the monitored result in the storage device 400 to construct a database and/or may upload the database to a cloud.

When the vehicle enters a wake-up mode, the wake-up mode controller 160 may control the intra-vehicle device 600 in a wake-up mode. In other words, when the vehicle enters the wake-up mode, the wake-up mode controller 160 may turn on the light device 640 to operate sunrise simulation lighting and release a shade mode. Further, the wake-up mode controller 160 may control the sound device 650 to output an alarm sound or a natural sound (e.g., wind, waves, the sound of a bird, or the like). The wake-up mode controller 160 may operate a massage device (not shown) of the seat 610. The wake-up mode controller 160 may control the diffuser device 630 to generate a wake-up scent. The wake-up mode controller 160 may control the air conditioning device 620 to generate cold wind.

The communication device 200 may receive sleep information or a target sleep time from the user terminal 500.

The input device 300 may receive a target sleep time, sleep information, and a destination from the user.

The storage device 400 may store a target sleep time, sleep information, and information about a route to a destination.

The intra-vehicle device 600 may include the seat 610, the air conditioning device 620, the diffuser device 630, the light device 640, the sound device 650 and the like.

Figure 2:
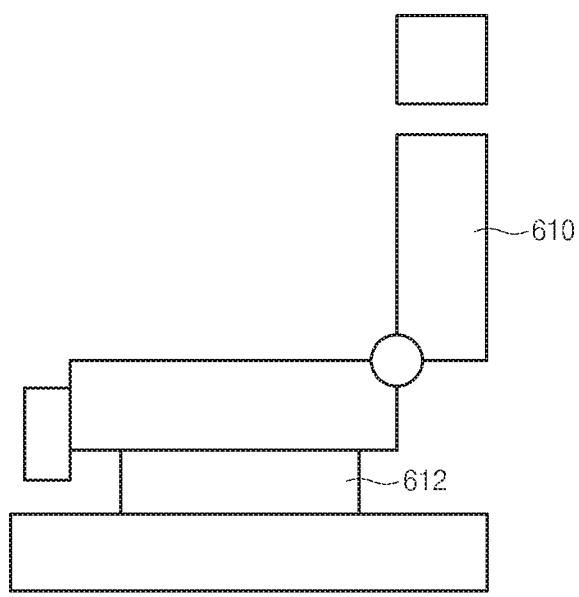
FIG. 2 is a drawing illustrating an example of a seat in a normal mode according to exemplary embodiments of the present disclosure.
Figure 3:
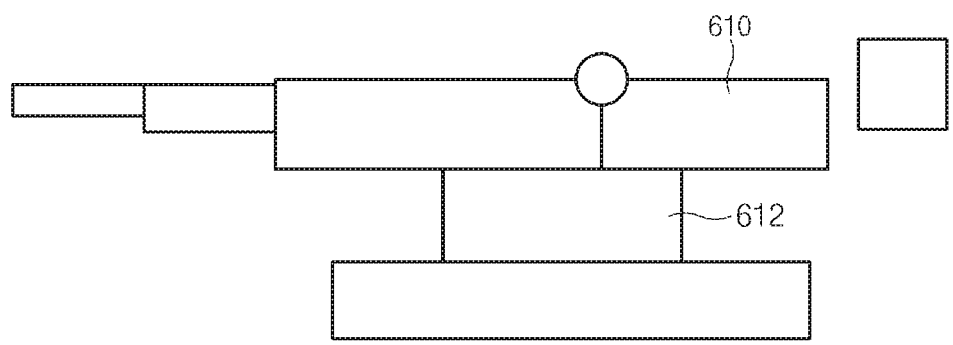
FIG. 3 is a drawing illustrating an example of a seat in a sleep mode according to exemplary embodiments of the present disclosure.
Figure 4:
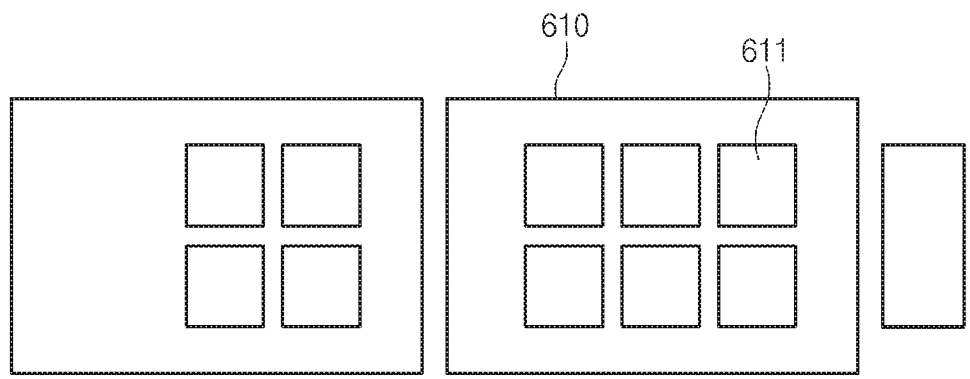
FIG. 4 is a drawing illustrating an example of pressure sensors located in a surface of a seat according to exemplary embodiments of the present disclosure.

FIG. 2 is a drawing illustrating an example of a seat in a normal mode according to exemplary embodiments of the present disclosure. FIG. 3 is a drawing illustrating an example of a seat in a sleep mode according to exemplary embodiments of the present disclosure. FIG. 4 is a drawing illustrating an example of pressure sensors located in a surface of a seat according to exemplary embodiments of the present disclosure.

Referring to FIG. 2, a damper may be fixed in a normal mode rather than a sleep mode. Referring to FIG. 3, since a seat is flattened in the sleep mode, a user may lie down and sleep conveniently and comfortably. In this case, the user may sleep conveniently and comfortably by offsetting movements of a vehicle using a 3-axis movement offsetting damper 612.

Referring to FIG. 4, when a seat 610 is flattened, pressure sensors 611 may be arranged. The plurality of pressure sensors 611 may be installed in a seat portion and a backrest of the seat 610 to monitor a quality of sleep of the user. In other words, the plurality of pressure sensors 611 may provide a change of pressure according to the tossing and turning of the user to a wake-up mode determining device 150 of FIG. 1 such that the wake-up mode determining device 150 may monitor a quality of sleep of the user. In this case, a radar, an ultrasonic sensor, and the like other than the pressure sensors 611 may be installed to monitor tossing and turning, breathing, heartbeat and the like of the user.

Figure 5:
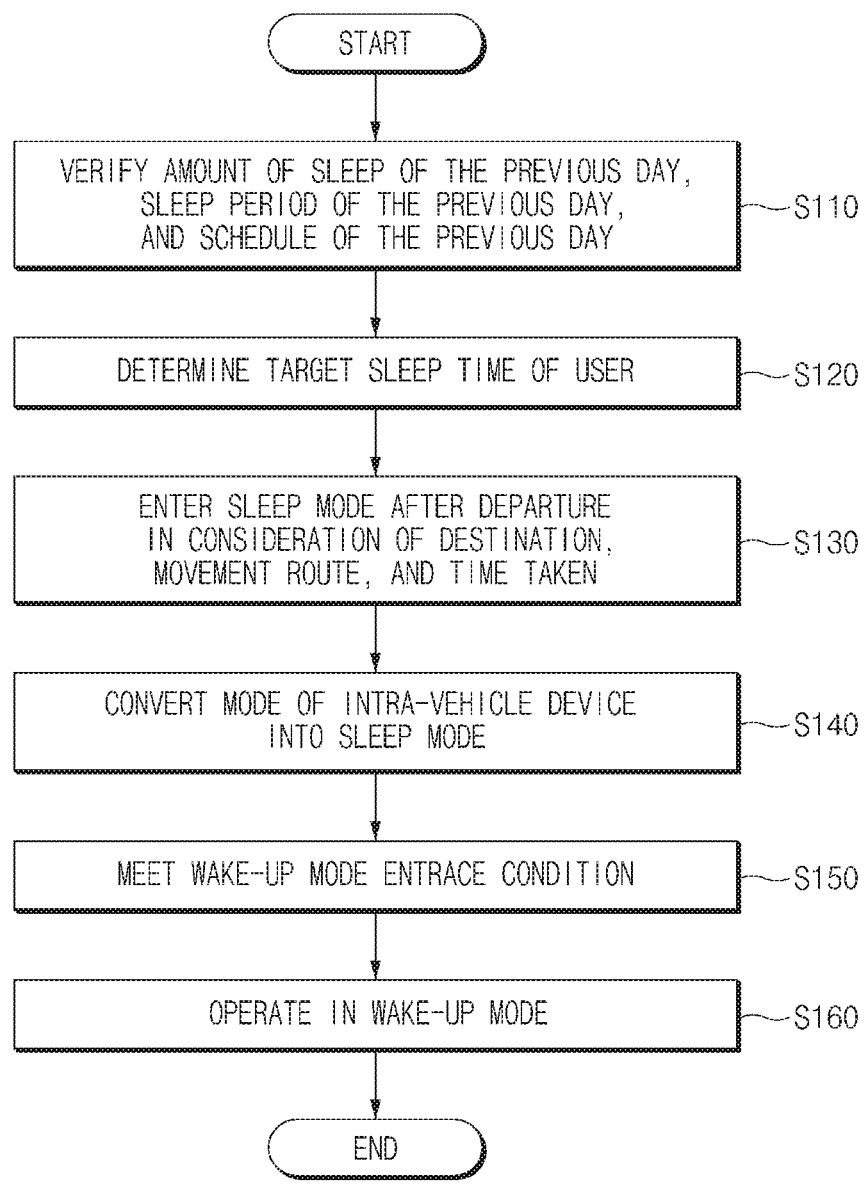
FIG. 5 is a flowchart illustrating a sleep aid method for a vehicle according to exemplary embodiments of the present disclosure.

Hereinafter, a description will be given in detail of a sleep aid method for a vehicle according to exemplary embodiments of the present disclosure with reference to FIG. 5. FIG. 5 is a flowchart illustrating a sleep aid method for a vehicle according to exemplary embodiments of the present disclosure.

In operation S110, a sleep aid device 100 for a vehicle of FIG. 1 may verify sleep information such as an amount of sleep of the previous day of the user, a sleep period of the previous day, and a schedule of the user's previous day. In this case, the sleep information such as the amount of sleep of the previous day, the sleep period of the previous day, and the schedule of the previous day may be received through data measured or input via a wearable device and a smart bed of the user or may be directly input via a smartphone when the user rides in a vehicle.

In operation S120, the sleep aid device 100 may set a target sleep time of the user. In this case, if there is a value previously input by the user, the sleep aid device 100 may set the target sleep time by using the value without change. If there is no value previously input for the target sleep time, the sleep aid device 100 may use a recommendation value in consideration of an age, gender, and the like of the user.

In operation S130, the sleep aid device 100 may establish a movement route through a destination, may determine a sleep-inducing time based on the movement route and a time required, and may enter a sleep mode. In this case, the sleep-inducing time may be determined in consideration of a time required to reach the destination and the target sleep time. If a destination arrival time is shorter than the target sleep time, the sleep aid device 100 may change a route to increase the destination arrival time. For example, if the target sleep time is three hours and if the time required to reach the destination is two hours, the sleep aid device 100 may search for a route for driving for three hours again and may establish a route to induce the user to wake up if three hours elapses after the user continuously maintain his or her sleep after the vehicle stops or parks. Further, the sleep aid device 100 may search a previously stored database for an optimal sleep route.

In operation S140, the sleep aid device 100 may convert a mode of an intra-vehicle device into a sleep mode. In operation S150, the sleep aid device 100 may monitor a sleep state of the user and may check whether the monitored sleep state meets a sleep mode entrance condition.

If the monitored sleep state meets the sleep mode entrance condition, in operation S160, the sleep aid device 100 may operate the intra-vehicle device in a wake-up mode.

Figure 6:
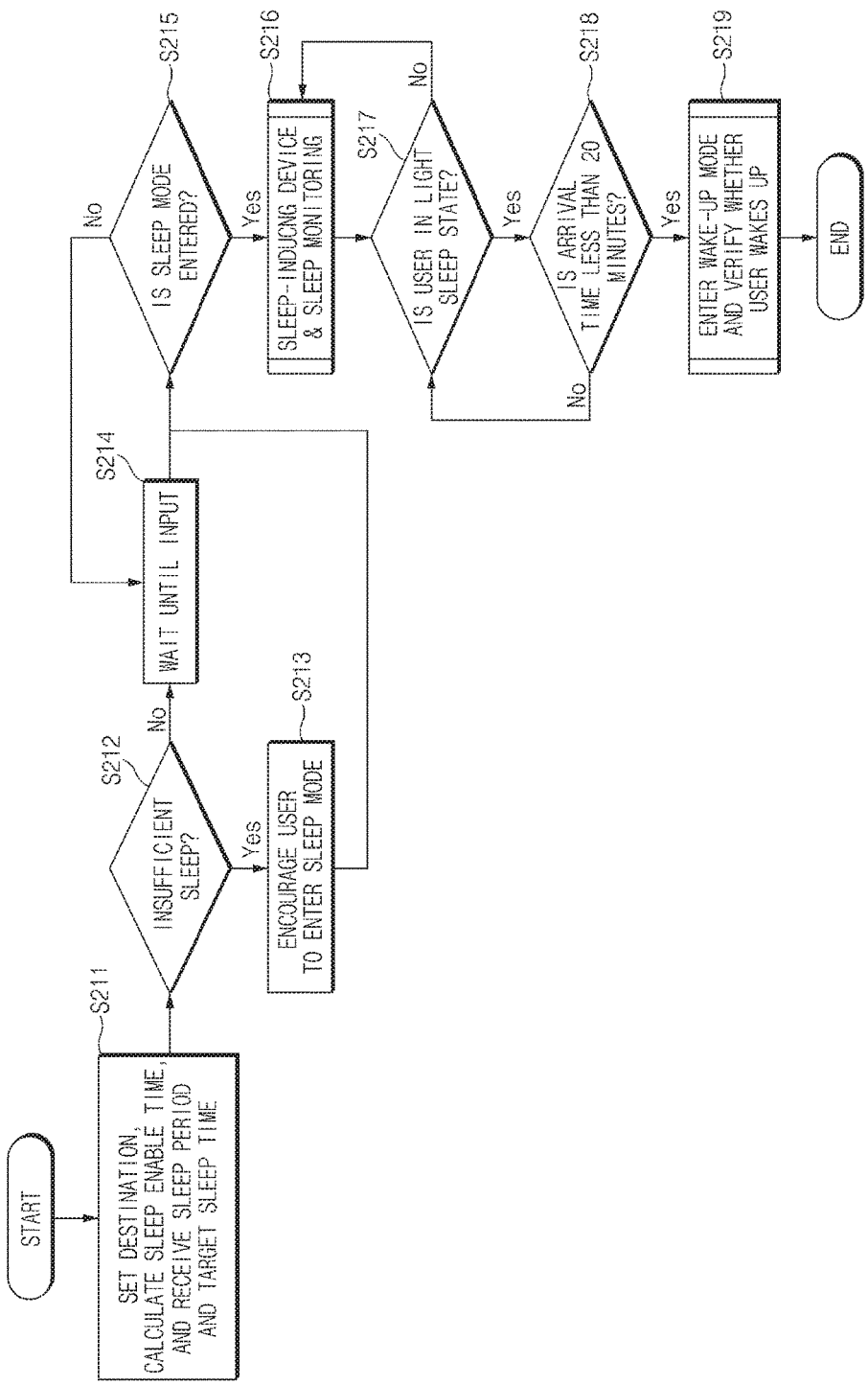
FIG. 6 is a flowchart illustrating a sleep aid method for a vehicle according to exemplary embodiments of the present disclosure.

Hereinafter, a description will be given in more detail of a sleep aid method for a vehicle according to exemplary embodiments of the present disclosure with reference to FIG. 6. FIG. 6 is a flowchart illustrating a detailed sleep aid method for a vehicle according to exemplary embodiments of the present disclosure.

In operation S211, a sleep aid device 100 for vehicle of FIG. 1 may receive a destination, may establish a route, and may receive or calculate a sleep enable time, a sleep period, and a target sleep time. In operation S212, the sleep aid device 100 may determine whether a user is in an insufficient sleep state to determine whether to enter a sleep mode.

If the user is in the insufficient sleep state, in operation S213, the sleep aid device 100 may encourage the user to enter the sleep mode. In operation S215, the sleep aid device 100 may determine whether the sleep mode is entered.

When the sleep mode is entered, in operation S216, the sleep aid device 100 may convert a mode of an intra-vehicle device 600 of FIG. 1 into the sleep mode to induce the user to sleep and may monitor a sleep state of the user using a variety of sensors.

In operation S217, the sleep aid device 100 may check whether the user is in a light sleep state. If the user is in the light sleep state, the sleep aid device 100 may determine whether an arrival time to the destination is less than 20 minutes. If the arrival time to the destination is less than 20 minutes, in operation S219, the sleep aid device 100 may enter a wake-up mode and may verify whether the user wakes up. In other words, the sleep aid device 100 may verify whether the user wakes up after inducing him or her to wake up. If the user wakes up, the sleep aid device 100 may end the wake-up mode.

Meanwhile, if the user is not in the insufficient sleep state in operation S212, in operation S214, the sleep aid device 100 may maintain an input waiting state to receive a request to enter the sleep mode. Hereafter, if the sleep aid device receives 100 the request to enter the sleep mode, the sleep aid device 100 may enter the sleep mode.

The present technology may help the user to engage in a deep sleep during movement using an autonomous vehicle and may aid the user in waking up at a time set to a target time in a light sleep state such that he or she may maintain the best condition.

Further, exemplary embodiments of the present disclosure may increase an effective value of the autonomous vehicle by implementing a specialized sleep-inducing function of the autonomous vehicle and may increase satisfaction of the user by enhancing quality of sleep of the user during a movement time.

Figure 7:
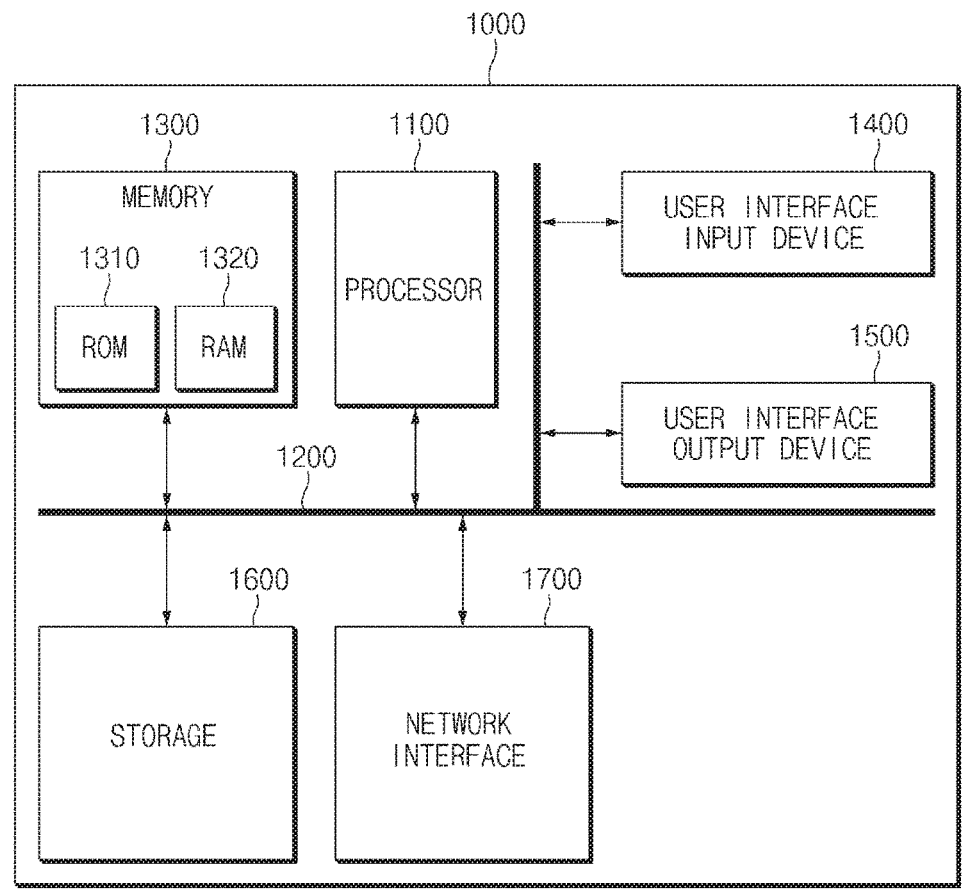
FIG. 7 is a block diagram illustrating a configuration of a computing system to which a sleep aid method for a vehicle is applied, according to exemplary embodiments of the present disclosure.

FIG. 7 is a block diagram illustrating a configuration of a computing system to which a sleep aid method for a vehicle is applied, according to exemplary embodiments of the present disclosure.

Referring to FIG. 7, a computing system 1000 may include one processor 1100, a memory 1300, a user interface input device 1400, a user interface output device 1500, a storage 1600, and a network interface 1700 which are connected with each other via a bus 1200.

The processor 1100 may be a central processing unit (CPU) or a semiconductor device for processing instructions stored in the memory 1300 and/or the storage 1600. Each of the memory 1300 and the storage 1600 may include various types of volatile or non-volatile storage media. For example, the memory 1300 may include a read only memory (ROM) and a random access memory (RAM).

Thus, the operations of the methods or algorithms described in connection with the embodiments disclosed in the specification may be directly implemented with a hardware module, a software module, or combinations thereof, executed by the processor 1100. The software module may reside on a storage medium (e.g., the memory 1300 and/or the storage 1600) such as a RAM, a flash memory, a ROM, an erasable and programmable ROM (EPROM), an electrically EPROM (EEPROM), a register, a hard disc, a removable disc or a compact disc-ROM (CD-ROM).

An exemplary storage medium may be coupled to the processor 1100. The processor 1100 may read out information from the storage medium and may write information in the storage medium. Alternatively, the storage medium may be integrated with the processor 1100. The integrated processor and storage medium may reside in an application specific integrated circuit (ASIC). The ASIC may reside in a user terminal. Alternatively, the integrated processor and storage medium may reside as a separate component of the user terminal. Further, the sleep aid device 100 may be implemented with a hardware processor and instructions, and the execution of the instructions causes the processor to perform various functions related to sleep aid control, including those described above.

The present technology may help the user to take, or engage in, deep sleep during movement of an autonomous vehicle and may aid the user in waking up in a light sleep state at a time set to a target time, allowing him or her to maintain the best condition, or receive deeper or increased amounts of sleep.

While the present disclosure has been described with reference to exemplary embodiments, it will be apparent to those skilled in the art that various changes and modifications may be made without departing from the spirit and scope of the present disclosure.

Therefore, exemplary embodiments of the present disclosure are not limiting, but illustrative, and the spirit and scope of the present disclosure is not limited thereto. The spirit and scope and the present disclosure should be interpreted by the following claims, and it should be interpreted that all technical ideas which are equivalent to the present disclosure are included in the spirit and scope of the present disclosure.

What is claimed is:

1. A sleep aid device for a vehicle, the device comprising:
a sleep information setting device for setting sleep information and a target sleep time of a user;
a route establishing device for establishing a route to a destination and for calculating a time required to reach the destination;
a sleep mode determining device for determining whether a current mode is a sleep mode and for determining a sleep-inducing start time using the sleep information and the time required to reach the destination;
a sleep mode controller for controlling an intra-vehicle device in the sleep mode at the sleep-inducing start time;
a wake-up mode determining device for determining a sleep state of the user and entering a wake-up mode when the user is in a light sleep state; and
a wake-up mode controller for controlling the intra-vehicle device in the wake-up mode when the wake-up mode is entered.

2. The device of claim 1, wherein the sleep information comprises one or more of an amount of sleep of the user, a quality of sleep of the user and schedule information of the user.

3. The device of claim 1, wherein the sleep information setting device receives the sleep information via one or more of a wearable device, a smart bed and a smartphone, or wherein the sleep information setting device directly receives the sleep information from the user in the vehicle.

4. The device of claim 1, wherein the sleep information setting device calculates the target sleep time using the sleep information.

5. The device of claim 1, wherein the sleep information setting device receives the target sleep time in advance from the user, or wherein the sleep information setting device sets the target sleep time to a previously stored recommendation value according to an age or gender of the user if the target sleep time is not received in advance.

6. The device of claim 1, wherein the sleep mode determining device determines whether the sleep mode is entered using one or more of a quality of sleep of the previous day of the user, a sleep time of the previous day, a sleep period of the previous day and a schedule of the previous day.

7. The device of claim 1, wherein the route establishing device establishes the route again to adjust the time required in response to the target sleep time if the target sleep time is shorter than the time required.

8. The device of claim 1, wherein the route establishing device establishes a shortest-distance or shortest-time route to the destination in the sleep mode, which is a route established by first searching for a road which facilitates cruise control.

9. The device of claim 1, wherein the intra-vehicle device comprises at least one of a seat, an air conditioning device, a diffuser device, a light device or a sound device.

10. The device of claim 9, wherein the sleep mode controller:
flattens the seat;
controls the air conditioning device to set an indoor temperature of the vehicle to a sleep temperature;
controls the diffuser device to generate a sleep-inducing scent;
turns off the light device to control the light device in a shade mode; and/or
controls the sound device to output at least one of a white noise, a natural sound or a sleep-inducing beep sound.

11. The device of claim 1, wherein the wake-up mode determining device enters the wake-up mode if the vehicle will arrive at the destination within a time period and if the user is in the light sleep state.

12. The device of claim 9, wherein the wake-up mode controller:
  turns on the light device;
  controls the sound device to output an alarm sound or a natural sound;
  operates a massage device of the seat;
  controls the diffuser device to generate a wake-up scent; and/or controls the air conditioning device to generate cold wind when the wake-up mode is entered.

13. A sleep aid system for a vehicle, the system comprising:
  a communication device for receiving sleep information or a target sleep time from a user terminal;
  an input device for receiving the target sleep time, the sleep information and a destination from a user;
  a sleep aid device for establishing a route to the destination, for determining a sleep-inducing start time based on a time required to reach the destination and the target sleep time, for controlling an intra-vehicle device in a sleep mode at the sleep-inducing start time, for monitoring a sleep state of the user and a destination arrival time, and for controlling the intra-vehicle device in a wake-up mode if the vehicle will arrive at the destination within a time and if the user is in a light sleep state; and
  a storage device for storing the target sleep time, the sleep information and information about the route to the destination.

14. The system of claim 13, wherein the user terminal comprises one or more of a wearable device, a smartphone and a smart bed.

15. A sleep aid method for a vehicle, the method comprising:
  setting sleep information and a target sleep time of a user;
  establishing a route to a destination and calculating a time required to reach the destination;
  determining whether a current mode is a sleep mode and determining a sleep-inducing start time using the sleep information and the time required;
  controlling an intra-vehicle device in the sleep mode at the sleep-inducing start time;
  entering a wake-up mode if the vehicle will arrive at the destination within a time period and if the user is in a light sleep state; and
  controlling the intra-vehicle device in the wake-up mode when the wake-up mode is entered.

16. The method of claim 15, further comprising:
  receiving the sleep information or the target sleep time from a smart device of the user;
  directly receiving the sleep information or the target sleep time from the user; or
  using a previously stored recommendation value according to an age or gender of the user as the target sleep time.

17. The method of claim 15, wherein the step of determining whether the current mode is the sleep mode and the step of determining the sleep-inducing start time comprises:
  determining whether the sleep mode is entered, using one or more of quality of a past sleep of the user, a past sleep time, a past sleep period and a past schedule.

18. The method of claim 15, wherein the step of establishing the route to the destination and the step of calculating the time required to reach the destination comprises:
  establishing the route again to adjust the time required in response to the target sleep time if the target sleep time is shorter than the time required.

19. The method of claim 18, wherein the step of establishing the route to the destination and the step of calculating the time required to reach the destination comprises:
  establishing a shortest-distance or shortest-time route to the destination in the sleep mode established by first searching for a road which facilitates cruise control.

20. The method of claim 15, wherein the step of controlling the intra-vehicle device in the sleep mode comprises:
  flattening a seat;
  controlling an air conditioning device to set an indoor temperature of the vehicle to a sleep temperature;
  controlling a diffuser device to generate a sleep-inducing scent; and/or
  turning off a light device to control the light device in a shade mode.

\* \* \* \* \*